US00PP26524P3

(12) United States Plant Patent
Bacon

(10) Patent No.: US PP26,524 P3
(45) Date of Patent: Mar. 22, 2016

(54) APRICOT TREE NAMED 'SUAPRITWELVE'

(50) Latin Name: *Prunus armeniaca*
Varietal Denomination: Suapritwelve

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 129 days.

(21) Appl. No.: 13/998,498

(22) Filed: Nov. 6, 2013

(65) Prior Publication Data

US 2015/0128314 P1 May 7, 2015

(51) Int. Cl.
*A01H 5/08* (2006.01)

(52) U.S. Cl.
USPC ..... Plt./186

(58) Field of Classification Search
USPC ..... Plt./186
See application file for complete search history.

*Primary Examiner* — Keith Robinson

(74) *Attorney, Agent, or Firm* — Knobbe, Martens, Olson & Bear, LLP

(57) ABSTRACT

A new and distinct apricot variety, *Prunus armeniaca* cv. 'Suapritwelve' is characterized by having large fruit (averaging approximately 60 mm in diameter) with a high sugar content at 17 brix and smooth skin.

1 Drawing Sheet

Latin name of the genus and species claimed: *Prunus armeniaca.*

Variety denomination: 'Suapritwelve'.

BACKGROUND AND SUMMARY OF THE INVENTION

The present invention relates to a new and distinct variety of apricot tree, herein after referred to by the cultivar name 'Suapritwelve.' The new variety was first originated by hybridized in May 2009 by Terry A. Bacon as breeder number: 'AP1063'.

The new variety is characterized by having large fruit (averaging approximately 60 mm in diameter) with a high sugar content at 17 brix and smooth skin.

The seed parent is unknown, being from a collection of seed from hybrid seedlings. The pollen parent is also unknown (open-pollinated). The parent varieties were first crossed in February 2006, with the date of first sowing being February 2007 and the date of first flowering being February 2009. The new apricot variety 'Suapritwelve' was first asexually propagated by Terry Bacon near Wasco, Kern County, Calif. in January 2010 by grafting.

The new variety 'Suapritwelve' most closely resembles 'Suaprieight' (U.S. Plant Pat. No. 10,232) but the fruit of the new variety has a higher sugar level at 17 brix, compared to 15 brix for 'Suaprieight' (U.S. Plant Pat. No. 10,232). Additionally, the new variety 'Suapritwelve' has a smoother skin than 'Suaprieight' (U.S. Plant Pat. No. 10,232). This makes the new variety more suitable for packinghouse packlines, compared to the bumpy skin of 'Suaprieight' (U.S. Plant Pat. No. 10,232) which contributes to more marking on a packline.

The new variety 'Suapritwelve' has been shown to maintain its distinguishing characteristics through successive asexual propagations by, for example, grafting.

BRIEF DESCRIPTION OF THE PHOTOGRAPH

The accompanying color photographic illustration shows typical specimens of the foliage and fruit of the present new apricot variety 'Suapritwelve'.

The illustration shows the upper and lower surface of the leaves, a view of the fruit as a whole, and a sectional view of a fruit divided across its suture plane to show flesh color, pit cavity and the stone remaining in place in a 3 year old plant.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to 3 year old 'Suapritwelve' plants grown in the vicinity of Wasco, Kern County, Calif., during 2013 and is believed to apply to plants of the variety grown under similar conditions of soil and climate elsewhere.

TREE

General: (Measurements taken on 3 year old tree unless otherwise noted).

- *Tree size.*—Medium. Normal for most apricot varieties. Reaches a height of 3.5 meters with normal pruning.
- *Spread.*—3 meters.
- *Tree vigor.*—Medium. Growth of approximately 1.8 to approximately 2 meters height in the first growing season.
- *Tree growth.*—Semi-upright spreading.
- *Tree productivity.*—Productive.
- *Tree form.*—Vase formed.
- *Bearer.*—Regular.
- *Fertility.*—Unknown.

*Branching.*—Medium.

*Tree canopy density.*—Medium. Pruning is required to open tree vase shape, allowing more sunlight to center of tree.

*Tree hardiness.*—Hardy in all fruit growing areas of California. Winter chilling requirement is approximately 550 hours at or below 7.2° C.

*Tree disease resistance/susceptibility.*—No specific testing for plant disease resistance/susceptibility has been undertaken. Under close observation in the vicinity of Wasco, Kern County, Calif., no particular plant/fruit disease resistance/susceptibility has been observed.

Trunk: (Measurements at 30 cm above soil line).

*Trunk diameter.*—Approximately 21 cm.

*Trunk texture.*—Smooth to slightly shaggy.

*Trunk color.*—About Medium Greyed-Green 197D in exposed areas to Dark Greyed-Orange 166A in recesses, becoming darker with age.

Branches: (Measurements at approximately 90 cm above soil line).

*Branch diameter.*—Approximately 9 cm.

*Branch texture.*—Smooth on 1$^{st}$ year wood, increasing roughness with tree age.

*Branch color.*—Branches vary from about Medium Greyed-Green 197D to Medium Greyed-Green 197B in exposed areas and Medium Greyed-Orange 165B in recesses.

*Branch lenticels.*—Few. Size: Medium. Density (no./cm$^2$): Variable, about 5. Color: About Dark Greyed-White 156A. Typical size: Approximately 4 mm in length and approximately 2 mm wide.

Flowering shoots: (Data taken in July at midpoint of current-season growth. Color and sizes described may vary due to differences in sunlight, vigor and temperatures.).

*Flowering shoot size.*—Average diameter: approximately 8 mm.

*Flowering shoot color.*—Topside: About Dark Greyed-Orange 165A. Underside: About Dark Greyed-Orange 165A.

*Flowering shoot lenticels.*—Size: Medium, about 10/cm2. Color: About Dark Greyed-White 156A. Diameter: Approximately 0.5 mm. Texture: Smooth.

*Flowering shoot leaf buds.*—Shape: Ovoid. Width: Approximately 1.5 mm. Length: Approximately 2 mm. Color: About Dark Greyed-Orange 165A. Texture: Smooth.

*Flowering shoot flower buds.*—Shape: Elongated ovoid. Width: Approximately 1.5 mm. Length: Approximately 4 mm. Color: About Dark Greyed-Orange 165A. Number: Usually 2. Texture: Smooth.

*Internode length.*—Medium and variable, approximately 1-4 cm midway on flowering shoots. Width: About 5 mm. Texture: Smooth.

*Density of buds.*—Medium.

*Distribution.*—Generally isolated on spurs and one year old shoots and older wood.

*Ratio of wood (leaf) bud to flowering shoots.*—1/2.

Root:

*Habit.*—Branching.

*Color.*—About White 155A.

*Time it takes to initiate roots.*—10 days.

*Time it takes to produce a rooted plant.*—6 weeks.

FOLIAGE

Leaves: (Data taken in July on fully expanded leaf at midpoint of current-season growth. Color and sizes described may vary due to differences in sunlight, vigor and temperatures).

*Leaf size.*—Medium. Length: Medium, approximately 7 cm. Width: Medium, approximately 5.5 cm.

*Leaf thickness.*—Medium.

*Leaf color.*—Upper surface: About Dark Green 135A. Lower surface: About Medium Green 136C.

*Leaf form.*—Circular.

*Leaf tip.*—Cuspidate.

*Leaf base.*—U-shaped.

*Leaf margin.*—Crenate.

*Venation.*—Pinately net veined.

*Vein color.*—About Light Green 138C.

*Leaf surface texture.*—Smooth (upper and lower).

*Leaf blade (ratio length/width).*—Small.

*Shape in cross section.*—Flat.

*Angle at apex.*—Medium.

*Profile.*—Flat.

*Leaf blade tip.*—Curved downwardly.

*Angle of tip.*—Acute.

*Undulation of margin.*—Slight.

Petiole:

*Length.*—Medium, approximately 25 mm.

*Diameter.*—Approximately 1 mm.

*Color.*—About Medium Green 138B, becoming Medium Red 42B in sunlight.

*Texture.*—Smooth (upper and lower).

Stipules:

*Number/leaf bud.*—Approximately 0 to 2.

*Typical length.*—Approximately 3 mm.

*Color.*—About Medium Green 139C.

*Persistence.*—Fall off.

*Texture.*—Smooth (upper and lower).

Glands:

*Form.*—Globose.

*Number.*—Approximately 0 to 3.

*Position.*—On petiole, alternate.

*Size.*—Medium, approximately 0.6 mm.

*Color.*—About Dark Greyed-Orange 165A.

FLOWERS

General:

*First bloom.*—February 22 in Wasco, Calif.

*Location of first bloom.*—Upper portion of the canopy.

*Full bloom.*—February 26 in Wasco, Calif.

*Location of full bloom.*—Middle of the canopy.

*Time of bloom.*—Medium, from approximately February 22-February 26 in Wasco, Calif.

*Duration of bloom.*—Medium, about 10 days.

*Diameter of fully open flower.*—Medium, Approximately 27 mm.

*Flower aroma.*—Very slight.

*Shape.*—Rosaceous.

Peduncle:

*Length.*—Medium, approximately 3 mm.

*Diameter.*—Medium, approximately 2 mm.

*Color.*—About Light Yellow-Green 145C, with highlights of about Medium Red 46D.

*Pubescence.*—Absent.

Petals:
*Number.*—5.
*Arrangement.*—Overlapping.
*Length.*—Approximately 12 mm.
*Diameter.*—Approximately 10 mm.
*Shape.*—Circular.
*Apex shape.*—Rounded.
*Base shape.*—Narrows at point of attachment.
*Color.*—Inner Surface: About Light Red 36D. Outer Surface: About Light Red 36D.
*Surface texture.*—Smooth (inner and outer).
*Margins.*—Smooth and slightly undulating.
*Frequency of flowers with double petals.*—None.
*Margin waviness.*—Weak.
*Base angle.*—Wide.
*Pubescence of inner surface.*—Absent.
*Pubescence of outer surface.*—Absent.

Sepals:
*Number.*—5.
*Length.*—Approximately 6 mm.
*Diameter.*—Approximately 4.5 mm.
*Shape.*—Broad ovate.
*Color.*—About Medium Red 42B.
*Surface texture.*—Smooth (inner and outer).
*Margins.*—Smooth, entire.
*Positioning.*—Adpressed to petals.
*Pubescence of inner surface.*—Absent.
*Pubescence of outer surface.*—Absent.
*Frequency of flowers with double sepals.*—None.

Stamens:
*Number.*—Approximately 20.
*Length.*—Approximately 11 mm.
*Filament color.*—About White 155A.
*Anther color.*—About Medium Yellow 14C.
*Pollen color.*—About Medium Yellow 14C.
*Position.*—Perigynous.
*Amount of pollen.*—Medium.

Pistil:
*Number.*—Usually one.
*Average length.*—Approximately 8 mm.
*Ovary diameter.*—Approximately 3 mm.
*Pubescence.*—Medium.
*Stigma extension in comparison to anthers.*—Below with anthers.
*Frequency of supplementary pistils.*—Few.

Receptacle:
*Depth.*—Medium, approximately 4 mm.
*Pubescence of inner surface* (*at pink bud stage*).—Absent.
*Pubescence of outer surface.*—Absent.

FRUIT (Data taken at firm-ripe on mature tree managed to obtain maximum quality under conditions stated in Description of Variety. Timing, colors and sizes described may vary due to differences in sunlight, vigor and temperatures).

General:
*Fruit harvest.*—Date of First Pick: Approximately May 24. Date of Last Pick: Approximately June 3.
*Date of description.*—Approximately May 28.
*Maturity when described.*—Firm.
*Season ripening.*—Medium.
*Position of maximum diameter.*—Towards the middle.
*Symmetry about the suture.*—Nearly symmetrical.

Fruit size:
*Length* (*stem end to apex*).—Approximately 60 mm.
*Diameter in line with suture plane.*—Approximately 60 mm.
*Diameter perpendicular to suture plane.*—Approximately 60 mm.
*Average weight.*—Approximately 112 gm.

Fruit form:
*Viewed from apex.*—Round, nearly symmetric.
*Viewed from side, facing suture.*—Rounded, nearly symmetric.
*Viewed from side, perpendicular to suture.*—Rounded, slightly asymmetric.

Fruit apex shape: Rounded, slightly indented at tip.

Fruit stem cavity:
*Shape.*—Rounded.
*Depth.*—Medium, approximately 1 cm.
*Breadth.*—Approximately 1.5 cm.

Fruit stem:
*Length.*—Medium, Approximately 8 mm.
*Diameter.*—Approximately 2 mm.
*Color.*—About Medium Green 143C.
*Adherence to stone.*—Medium.
*Texture.*—Smooth.

Fruit skin:
*Thickness.*—Medium.
*Adherence to flesh.*—Medium.
*Surface texture.*—Smooth to slightly irregular.
*Pubescence.*—Moderate to scant, short, does not need roll up when rubbed.
*Bloom.*—Slight.
*Ground color.*—About Light Orange-Red 31C.
*Overcolor.*—About Dark Red 45A.
*Taste.*—Slightly tart.
*Reticulation.*—Slight.
*Tendency to crack.*—Slight, in wet season.

Fruit flesh:
*Ripens.*—Evenly.
*Texture.*—Melting.
*Fibers.*—Few.
*Flavor.*—Sweet-mild.
*Brix.*—Approximately 17°.
*Juice.*—Moderate.
*Aroma.*—Medium-high.
*Color.*—About Medium Orange-Red 31A.
*Anthocyanin color under skin.*—Absent.
*Anthocyanin color of flesh.*—Absent.
*Anthocyanin color around stone.*—Absent.
*Acidity.*—Medium, 1.2%.
*Eating quality.*—Good.
*Stone/flesh ratio.*—4 g/112 g.
*Firmness.*—Medium.

Pit cavity size:
*Length.*—Approximately 25 mm.
*Diameter in line with suture plane.*—Approximately 25 mm.
*Diameter perpendicular to suture plane.*—Approximately 9 mm.
*Color.*—About Medium Orange-Red 31A.

Fruit use: Fresh market.

Fruit shipping/keeping quality: Medium.

Stone:
*Stone freeness.*—Cling, over entire surface.
*Degree of adherence to flesh.*—Medium.
*Size.*—Medium.

*Size compared to fruit.*—Small.
*Length.*—Medium, approximately 25 mm.
*Suture.*—Slightly sunken.
*Diameter in line with suture plane.*—Approximately 25 mm.
*Diameter perpendicular to suture plane.*—Approximately 9 mm.
*Angle of stalk end.*—Obtuse.
*Stone form* (*viewed from side*).—Round.
*Stone form* (*viewed from stem end*).—Oval, narrow.
*Stone form* (*viewed from ventral end*).—Flattened.
*Stone base shape.*—Rounded.
*Stone apex shape.*—Nearly rounded.
*Hilum.*—Narrow.
*Stone surface.*—Slightly pitted with a few ridges extending the length.
*Stone halves.*—Nearly equal.
*Stone ridges.*—Continuous.
*Stone outgrowing keel.*—Partly developed.
*Stone tendency to split.*—Rare.
*Stone color.*—About Medium Greyed-Orange 174B.
*Position of maximum.*—Middle.
*Sides.*—Nearly equal.
*Pits.*—Shallow, irregular.
*Fibers.*—Retains short fiber-like threads along the ridges.
*Ventrical edge.*—Thin with slight wing towards middle.
*Dorsal edge.*—Medium, continuous.

What is claimed is:

1. A new and distinct variety of apricot tree named 'Suapritwelve' as herein illustrated and described.

* * * * *

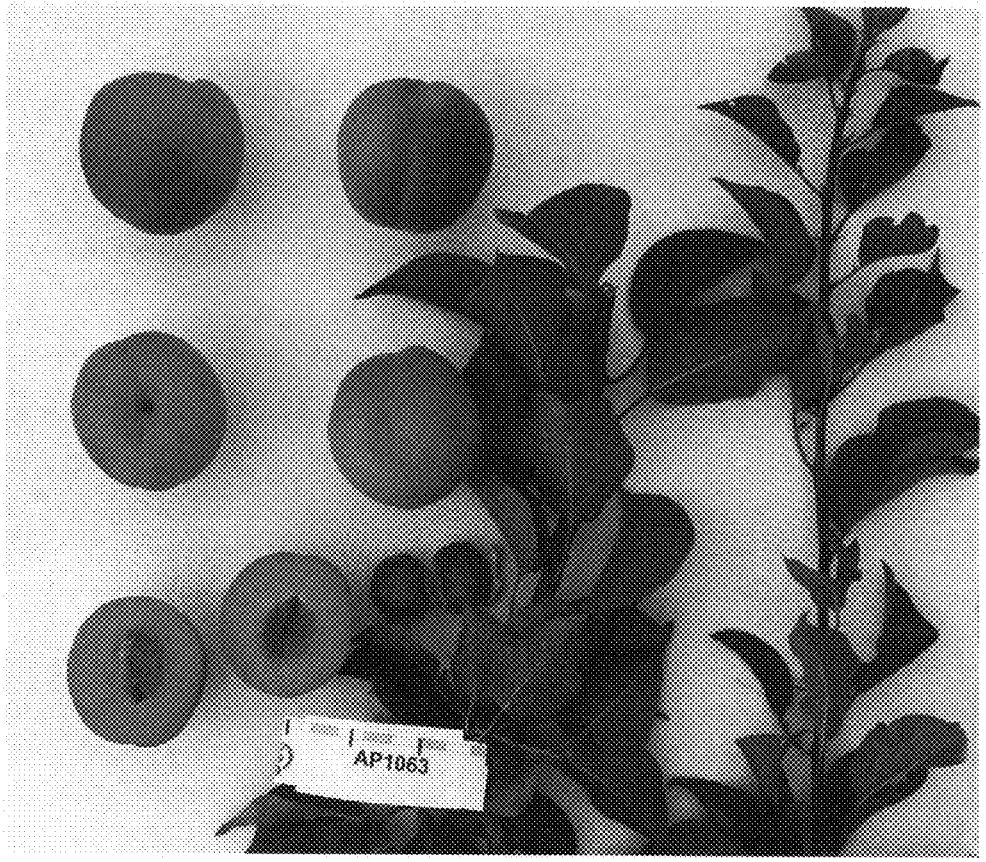
AP1063